US009733232B1

(12) United States Patent
Stolovitzky et al.

(10) Patent No.: US 9,733,232 B1
(45) Date of Patent: Aug. 15, 2017

(54) NANOPILLAR ARRAYS WITH INTERFACES FOR CONTROLLED POLYMER STRETCHING AND EFFECTIVE TRANSLOCATION INTO NANOCHANNELS

(71) Applicant: International Business Machines Corporation, Armonk, NY (US)

(72) Inventors: Gustavo A. Stolovitzky, Riverdale, NY (US); Chao Wang, Chandler, AZ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/005,576

(22) Filed: Jan. 25, 2016

(51) Int. Cl.
| | |
|---|---|
| *G01N 21/64* | (2006.01) |
| *G01N 1/16* | (2006.01) |
| *B01L 3/00* | (2006.01) |
| *G01N 33/487* | (2006.01) |

(52) U.S. Cl.
CPC .... *G01N 33/48721* (2013.01); *B01L 3/50273* (2013.01); *B01L 3/502707* (2013.01); *B01L 3/502715* (2013.01); *B01L 3/502761* (2013.01); *B01L 2200/027* (2013.01); *B01L 2200/0663* (2013.01); *B01L 2300/0816* (2013.01); *B01L 2300/0877* (2013.01); *B01L 2300/0896* (2013.01); *B01L 2400/086* (2013.01)

(58) Field of Classification Search
CPC ............. B01L 3/00; G01N 21/64; G01N 1/16
USPC .......................................... 422/502; 436/165
See application file for complete search history.

(56) References Cited

U.S. PATENT DOCUMENTS

| | | | |
|---|---|---|---|
| 5,872,010 A | * | 2/1999 | Karger ................. B01J 19/0093 |
| | | | 204/451 |
| 6,454,924 B2 | | 9/2002 | Jedrzejewski et al. |
| 7,217,562 B2 | | 5/2007 | Cao et al. |
| 7,586,091 B2 | * | 9/2009 | Takahashi ......... B01L 3/502753 |
| | | | 204/451 |
| 7,670,770 B2 | | 3/2010 | Chou et al. |
| 7,928,368 B2 | * | 4/2011 | Nissila .................. H01J 49/167 |
| | | | 250/281 |

(Continued)

OTHER PUBLICATIONS

Chan, et al., "Effects of Embedded Sub-Micron Pillar Arrays in Microfluidic Channels on Large DNA Electrophoresis," Electrophoresis 2009, 30, pp. 3242-3249.

(Continued)

*Primary Examiner* — Arlen Soderquist
(74) *Attorney, Agent, or Firm* — Cantor Colburn LLP; Vazken Alexanian

(57) ABSTRACT

A technique relates to stretching an extensible molecule. The molecule moves through an array of pillars in a flow direction, where the array has an interface connecting a first pillar region and a second pillar region. Stretching the molecule by traversing the molecule in the flow direction through the interface connecting the first pillar region to the second pillar region, such that a first end and a second end of the molecule straddle a straddle pillar, thereby causing the first end to extend along a first path in the second and the second end to extend along a second path. Traversing the molecule stretches the first end and the second end along two different paths. The molecule is further traversed through the array such that the second end follows the first end along the first path, where the stretching causes the molecule to be in an uncoiled state.

19 Claims, 14 Drawing Sheets

(56) References Cited

U.S. PATENT DOCUMENTS

| | | | |
|---|---|---|---|
| 8,333,934 B2 | 12/2012 | Cao et al. | |
| 8,545,772 B2 | 10/2013 | Kanigan et al. | |
| 8,722,327 B2 | 5/2014 | Cao et al. | |
| 9,533,879 B2* | 1/2017 | Cao | B81C 1/00119 |
| 2001/0036669 A1* | 11/2001 | Jedrzejewski | B01J 19/0046 436/94 |
| 2003/0049563 A1* | 3/2003 | Iida | B01L 3/502761 430/296 |
| 2004/0033515 A1* | 2/2004 | Cao | B01L 3/502707 435/6.12 |
| 2006/0065528 A1* | 3/2006 | Lopez | G01N 27/44791 204/450 |
| 2010/0288689 A1* | 11/2010 | Zhu | B01D 61/147 210/336 |
| 2011/0034339 A1 | 2/2011 | Goyal | |
| 2011/0296903 A1* | 12/2011 | Cao | B01L 3/502761 73/64.56 |
| 2012/0328488 A1 | 12/2012 | Puntambekar et al. | |
| 2013/0172671 A1* | 7/2013 | Rentschler | B32B 25/20 600/109 |

OTHER PUBLICATIONS

Chao Wang, et al., "Hydrodynamics of Diamond-Shaped Gradient Nanopillar Arrays for Effective DNA Translocation into Nanochannels," ACS, NANO, vol. 9, No. 2, Jan. 27, 2015, pp. 1206-1218.

Das, et al., "Single Molecule Linear Analysis of DNA in Nano-Channel Labeled with Sequence Specific Fluorescent Probes," Nucleic Acids Res. 2010, 38, pp. e177.

Fu, J. P, et al., "A patterned Anisotropic Nanofluidic Sieving Structure for Continuous-Flow Separation of DNA and Proteins," Nat. Nanotechnol. 2007, 2, pp. 121-128.

Grosberg, et al., "DNA Capture into a Nanopore: Interplay of Diffusion and Electrohydrodynamics," The Journal of Chemical Physics, 2010,133, pp. 165102.

Han Cao, et al., "Gradient nanostructures for interfacing microfluidics and nanofluidics," Applied Physics Letters, vol. 81, No. 16, Oct. 14, 2002, pp. 3058-3060.

Han, J, et al., "Separation of Long DNA Molecules in a Microfabricated Entropic Trap Array," Science 2000, 288, pp. 1026-1029.

Huang, et al., "Continuous Particle Separation Through Deterministic Lateral Displacement," Science 2004,304, pp. 987-990.

Lam, E. T, et al., "Genome Mapping on Nanochannel Arrays for Structural Variation Analysis and Sequence Assembly," Nat Biotech 2012, 30, pp. 771-776.

Levy, S. L., et al., "Entropic Unfolding of DNA Molecules in Nanofluidic Channels," Nano Lett. 2008, 8, pp. 3839-3844.

Liang, X. G., et al., "Nanogap Detector inside Nanofluidic Channel for Fast Real-Time Label-Free DNA Analysis," Nano Lett. 2008, 8, pp. 1472-1476.

Margulies, et al., "Genome Sequencing in Microfabricated High-Density Picolitre Reactors," Nature 2005, 437, pp. 376-380.

Metzker, M. L., "Sequencing Technologies—the Next Generation," Nat Rev Genet., 2010, 11, pp. 31-46.

Muthukumar, M., "Theory of Capture Rate in Polymer Translocation," The Journal of Chemical Physics, 2010, 132, pp. 195101.

Perkins, T, et al. "Stretching of a Single Tethered Polymer in a Uniform Flow," Science 1995, 268, pp. 83-87.

Reisner, W., et al. "Statics and Dynamics of Single DNA Molecules Confined in Nanochannels," Phys. Rev. Lett. 2005, 94, pp. 196101.

Reisner, et al., "DNA Confinement in Nanochannels: Physics and Biological Applications," Rep. Prog. Phys. 2012, 75, pp. 106601.

Riehn, R, et al., "Restriction Mapping in Nanofluidic Devices," Proc. Natl. Acad. Sci. U. S. A. 2005,102, pp. 10012-10016.

Tegenfeldt, J. O., "The Dynamics of Genomic-Length DNA Molecules in 100-nm Channels," Proc. Natl. Acad. Sci. U. S. A. 2004, 101, pp. 10979-10109.

Tegenfeldt, J. O., et al. "Micro- and Nanofluidics for DNA Analysis," Anal. Bioanal. Chem. 2004, 378, pp. 1678-1692.

Turner, S., et al. "Confinement-Induced Entropic Recoil of Single DNA Molecules in a Nanofluidic Structure," Phys. Rev. Lett. 2002, 88, pp. 128103.

Viero, Y., et al., "Hydrodynamic Manipulation of DNA in Nanopost Arrays: Unhooking Dynamics and Size Separation," Small 2011, 7, pp. 3508-3518.

Zwolak, M., et al., "Colloquium: Physical Approaches to DNA Sequencing and Detection," Rev. Mod. Phys. 2008, 80, pp. 141-165.

* cited by examiner

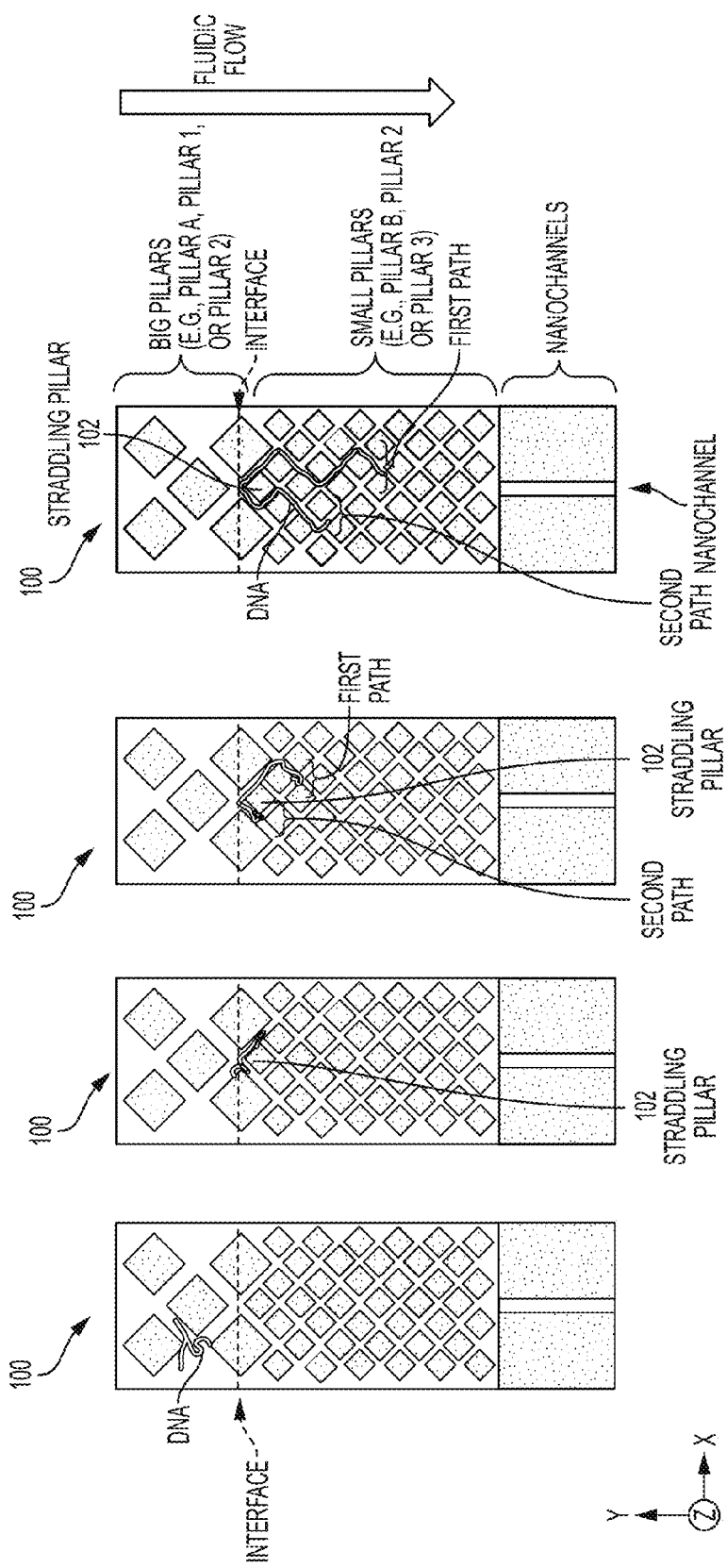

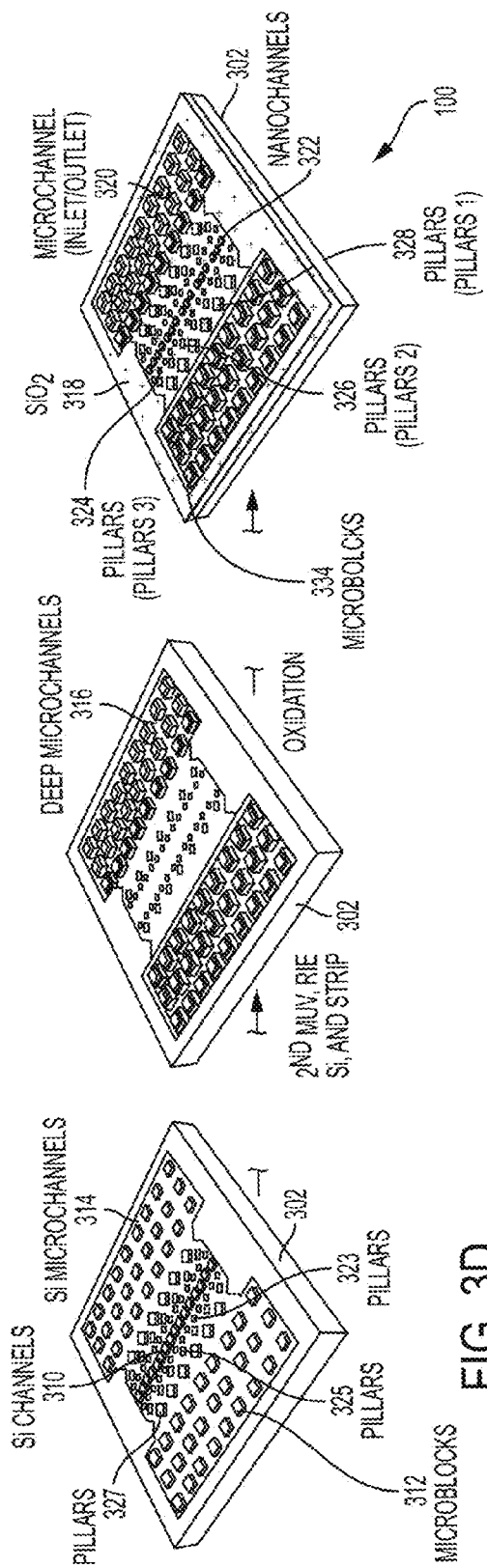

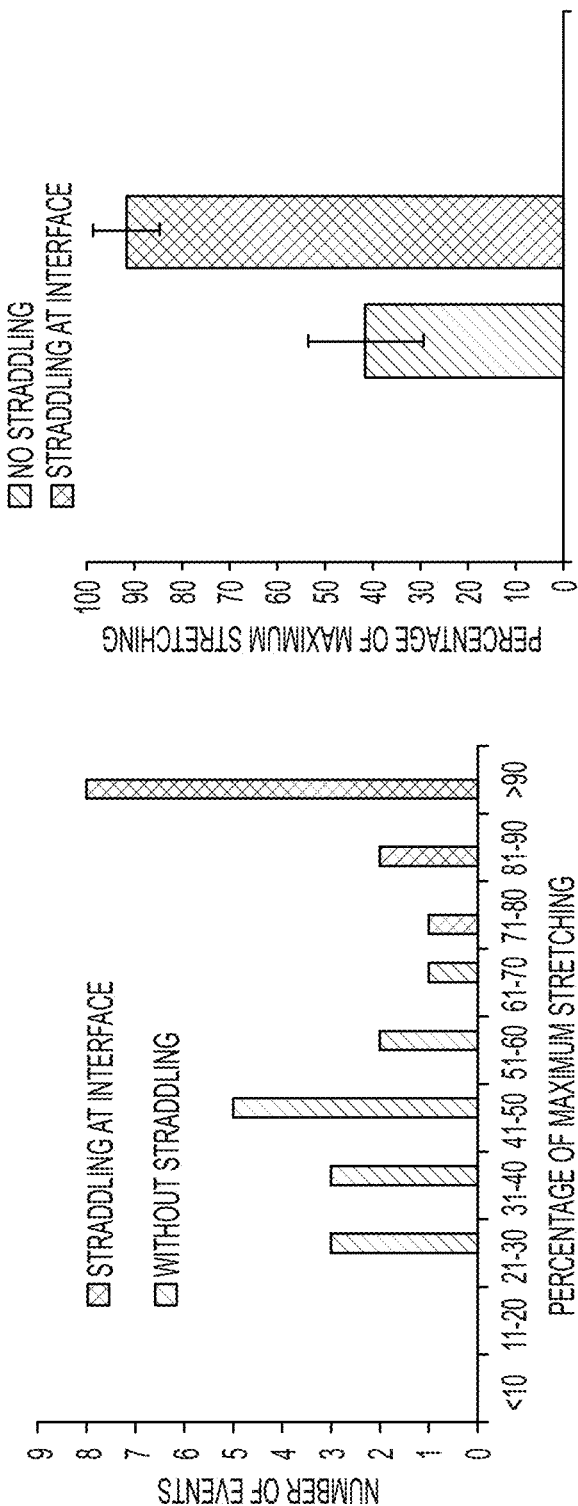

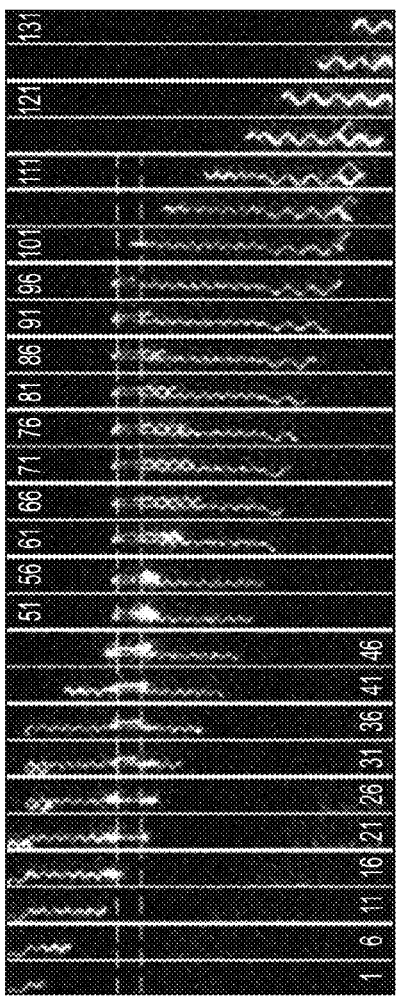
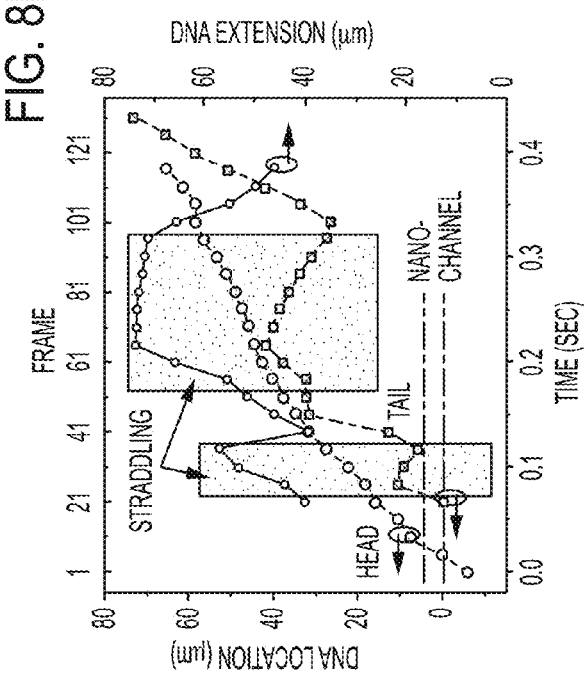
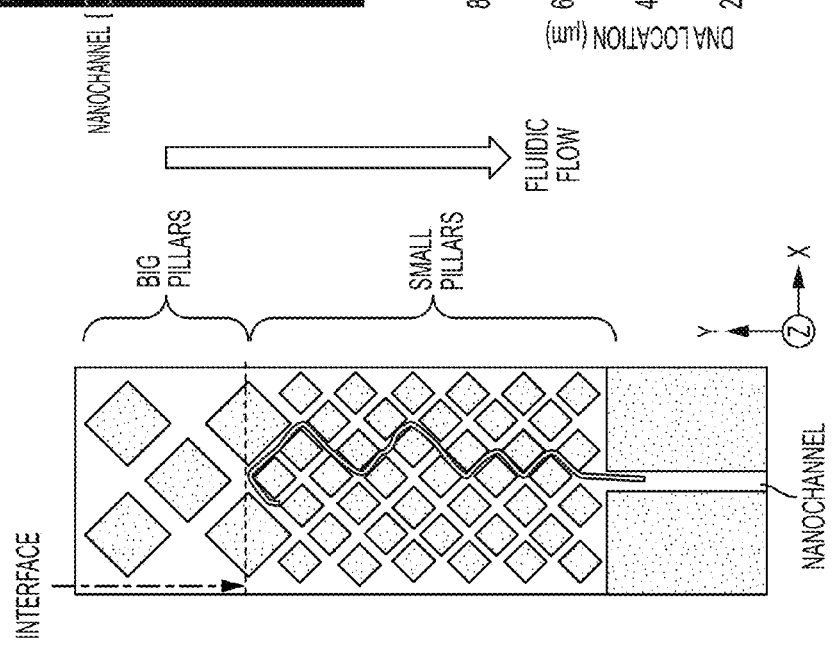
FIG. 8B
FIG. 8C
FIG. 8A

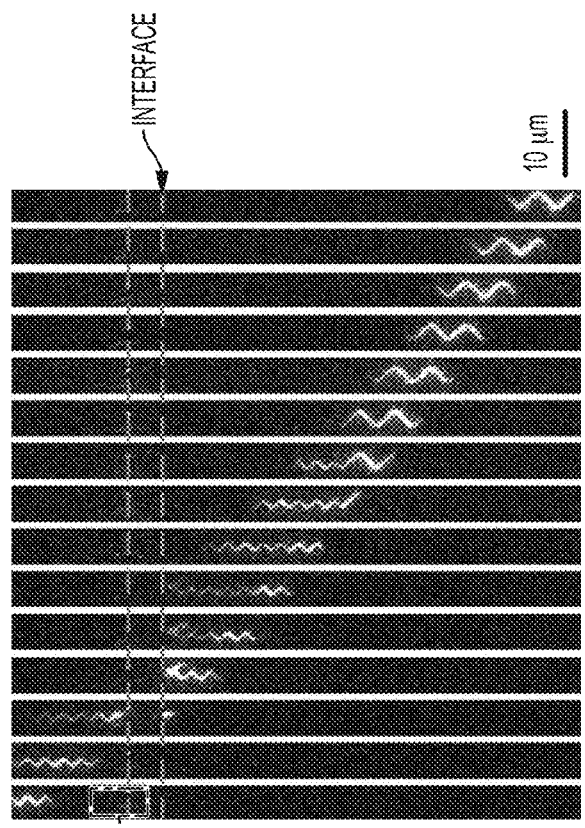
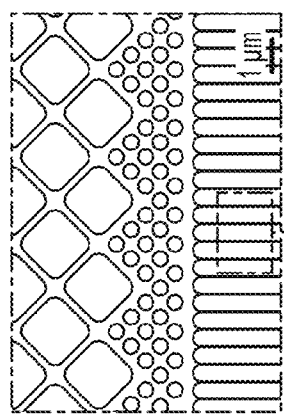
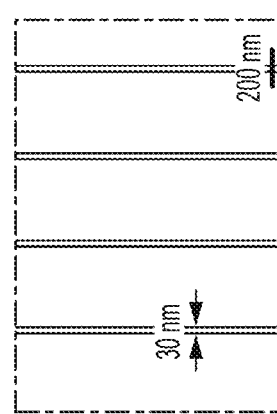
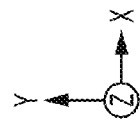
FIG. 9A
FIG. 9B
FIG. 9C

NANOPILLAR ARRAYS WITH INTERFACES FOR CONTROLLED POLYMER STRETCHING AND EFFECTIVE TRANSLOCATION INTO NANOCHANNELS

The following disclosure(s) are submitted under 35 U.S.C. 102(b)(1)(A): Hydrodynamics Of Diamond-Shaped Gradient Nanopillar Arrays For Effective DNA Translocation Into Nanochannels; Aughors: Chao Wang and Gustavo Stolovitsky; Publication Date (Web): Jan. 27, 2015; ACS Nano, 2015, 9 (2), pp 1206-1218; DOI: 10.1021/nn507350e, which is herein incorporated by reference in its entirety.

BACKGROUND

The present invention relates generally to the field of nanodevices, and more specifically, to diamond-shaped pillars in nanopillar arrays for controlled polymer stretching and in particular DNA stretching and effective translocation into nanochannels.

DNA (deoxyribonucleic acid) encodes rich genetic information that is closely linked to human health and critical to diagnosing predisposition to diseases, such as cancers. Over the past decade, tremendous technological advancement in DNA sequencing has made possible the fast and inexpensive retrieval of such information and thus revolutionized scientific understanding of genomics and biomedicine. Despite these achievements, one technological limitation of incumbent sequencing technologies that remains unresolved is the short DNA read length (<1000 bases), which increases error rate because of extensive sample fragmentation, modification, and amplification. Recently, advanced micro- and nanofluidic systems, e.g., nanochannels and nanopores, have been developed for the sorting, sensing, and analysis of DNA and have the potential of reading single long DNA molecules without elaborate sample preparation, thus potentially providing high information density and high sequence fidelity at a lower cost.

The issue regarding success for these nanochannel/pore technologies is the ability to linearize and translocate DNA macromolecules through a nanoconfined fluidic environment, where the critical genetic information can be retrieved by optical mapping and/or electrical detection. However, translocating a long strand of DNA into an extremely narrow nanochannel/pore is recognized to be challenging, because the entropy loss resulting from the confinement and the need to stretch the DNA macromolecule create a free energy barrier, which reduces DNA capture rates and causes clogging at the nanochannel/pore entrance.

SUMMARY

According to one embodiment, a method to stretch an extensible molecule flowing in a fluidic device is provided. The method includes moving a molecule through an array of pillars in a flow direction, where the array of pillars is organized to have at least one interface connecting a first pillar region and a second pillar region. The method includes stretching the molecule by traversing the molecule in the flow direction through the interface connecting the first pillar region to the second pillar region, such that a first end and a second end of the molecule straddle at least one straddle pillar, thereby causing the first end to extend in the flow direction along a first path in the second pillar region and causing the second end to extend in the flow direction along a second path in the second pillar region. Traversing the molecule stretches the first end and the second end along two different paths. Also, the method includes further traversing the molecule through the array of pillars in the flow direction such that the second end follows the first end along the first path in the second pillar region, where the stretching causes the molecule to be in an uncoiled state.

According to one embodiment, a method of fabricating an array of pillars to cause straddling is provided. The method includes forming a first pillar region of first pillars, where a gap separates the first pillars from one another. The method includes forming a second pillar region of second pillars such that the first and second pillar regions have an interface, where a smaller gap separates the second pillars from each other, and where the first pillars have a larger width than the second pillars. Also, the method includes forming an interface that is discontinuous between the first pillar region and the second pillar region, such that a point of the second pillars is positioned at the gap of the first pillars at the interface, where one or more of the second pillars, positioned at the gap of the first pillars, is configured to act as a straddling pillar.

According to one embodiment, a fluidic device having an array of pillars to cause straddling is provided. The device includes a first pillar region of first pillars, where a gap separates the first pillars from one another. The device includes a second pillar region of second pillars such that the first and second pillar regions have an interface, where a smaller gap separates the second pillars from each other, and where the first pillars have a larger width than the second pillars. Also, the device includes an interface that is discontinuous between the first pillar region and the second pillar region, such that a point of the second pillars is positioned at the gap of the first pillars at the interface, where one or more of the second pillars, positioned at the gap of the first pillars, is configured to act as a straddling pillar.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

FIG. 1A is a schematic of a nanopillar array to illustrate a coiled state of a DNA molecule before reaching the interface according to an embodiment.

FIG. 1B is a schematic of the nanopillar array depicting the start of straddling by the molecule to stretch the molecule according to an embodiment.

FIG. 1C is a schematic of the nanopillar array depicting the further straddling by the molecule to further stretch the molecule according to an embodiment.

FIG. 1D is a schematic of the nanopillar array depicting additional stretching of the molecule by straddling according to an embodiment.

FIGS. 3A, 3B, 3C, 3D, 3E, and 3F illustrate a fabrication scheme of an example nanopillar array according to an embodiment, in which:

FIG. 3A is a schematic of an intermediate structure illustrating an oxide layer disposed on a substrate;

FIG. 3B is a schematic of the intermediate structure illustrating a nanofluidic mask etched into the oxide layer;

FIG. 3C is a schematic of the intermediate structure illustrating disposing and patterning a photoresist mask;

FIG. 3D is a schematic of the intermediate structure illustrating use of the nanofluidic mask and photoresist mask to etch the substrate;

FIG. 3E is a schematic of the intermediate structure illustrating deep microchannels formed inside the shallow microchannel; and FIG. 3F is a schematic of the resultant nanopillar array with an oxide layer disposed on top.

FIG. 7A is a graph illustrating the probability of the percentage of maximum stretching for straddling at the interface versus no straddling according to an embodiment.

FIG. 7B is another graph illustrating the average percentage of maximum stretching for straddling at the interface versus no straddling according to an embodiment.

FIG. 8A is a schematic of a nanopillar array illustrating that straddling keeps the DNA molecule in stretched form, and facilitates DNA translocation and stretching in the nanochannel according to an embodiment.

FIG. 8B illustrates fluorescent images of the DNA molecule travelling through the nanopillar array according to an embodiment.

FIG. 8C is a graph of temporal hydrodynamic interaction and DNA extension in conjunction with the frames in FIG. 8B according to an embodiment.

FIG. 9A is a scanning electron microscope image of a nanopillar array according to an embodiment.

FIG. 9B is a scanning electron image of nanochannels in the nanochannel region of FIG. 9A according to an embodiment.

FIG. 9C illustrates consecutive fluorescence images showing DNA translocation according to an embodiment.

DETAILED DESCRIPTION

Figure 1E:
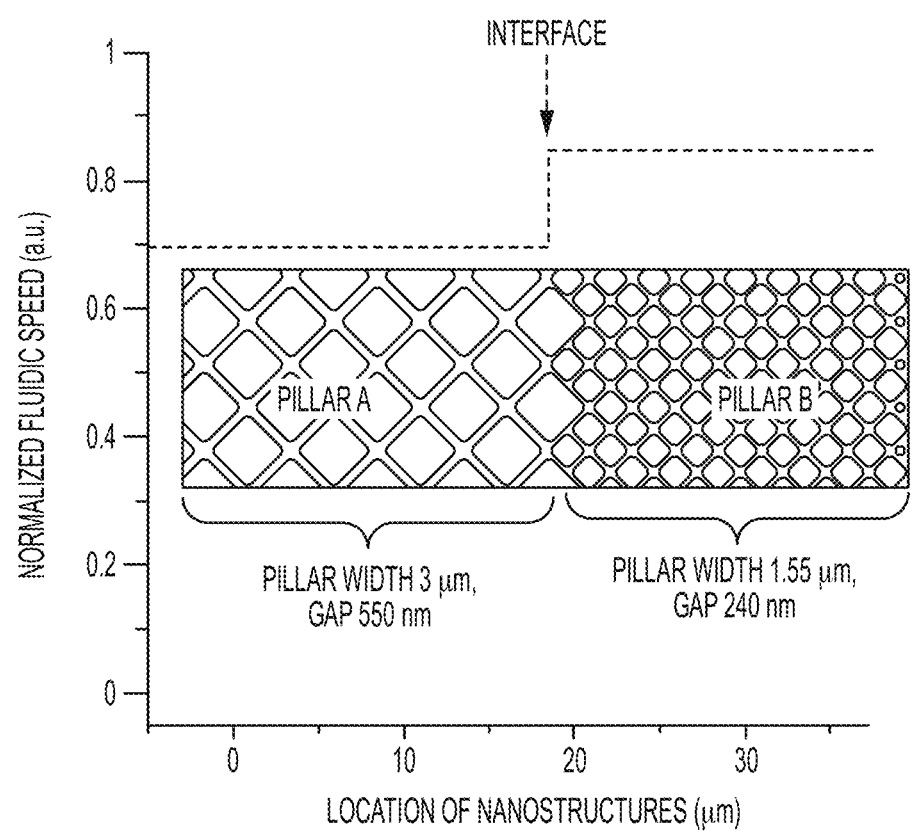
FIG. 1E is a graph illustrating an abrupt change in speed at the interface of a first pillar region and a second pillar region for FIGS. 1A, 1B, 1C, and 1D.

The crossing of a DNA molecule through a narrow nanochannel is slowed down by the entropic barrier caused by the need to uncoil the molecule. To catalyze the crossing of this entropic barrier, it is important to prestretch the DNA molecules. This can be achieved by nanopatterning features such as wider nanochannels or nanopillars. It has been recognized that such prestretching features should be patterned over a large area with a dimensional gradient from the micrometer to the nanometer regime and ultimately interface with the nanochannel/pore entrance. Nevertheless, it remains a challenge to design and implement complex nanofluidic structures, due to the stringent photolithographic requirements, and more particularly, an incomplete understanding of DNA hydrodynamic behavior in such fluidic systems. As a result, DNA dynamics is not clearly understood in nanochannel arrays. Further, state-of-the-art work demonstrated that a gradient of circular pillar arrays can reduce the entropic barrier at the nanochannel entrance.

Embodiments provide diamond-shaped nanopillars integrated in a planar fluidic system for location-specific DNA straddling. In experiments, 78% of 18 analyzed straddling events (67% of all DNA translocation events analyzed frame by frame and pixel by pixel) occurred at a designed pillar interface where the pillar width changes from 3 μm (in one pillar region) to 1.55 μm (in another pillar region). Such a high straddling occurrence rate and a location-specific behavior shows that nanopillars region interfaces can greatly alter the DNA hydrodynamic flow and induce controlled DNA stretching, according to embodiments. An event is an observation taken under microscope. For example, an event corresponds to molecules being analyzed.

Using single-molecule analysis, the particular DNA translocation parameters (e.g., speed and extension) are mapped to nanofluidic channels of different lengths and pillars of gradient dimensions. The mapping allows experimenters to visualize, for the first time, the impact of nanostructure geometries to the complex DNA hydrodynamic flow behavior in an integrated nanofluidic system.

Embodiments disclose how appropriately scaled diamond-shaped nanopillars participate in (1) guiding DNA into as small as 30 nanometer (nm) channels with minimized clogging, (2) stretching DNA to nearly 100% of their dyed contour length, (3) inducing location-specific straddling of DNA at nanopillar interfaces, and (4) modulating DNA speeds by pillar geometries. This provides a new perspective towards addressing particular challenges such as minimizing clogging and DNA pre-stretching in single-molecule DNA sequencing using ultra-small sensors (e.g., nanopores or nanochannels).

Dyed contour length of double-stranded DNA is approximately 30% longer than its length without dye labels because of dye insertion. For example, contour length (intrinsic) is the length at maximum physically possible extension. For DNA, the contour length (L) is $L=N \cdot d$. Here, N is the number of DNA base (or base pairs), and d is the spacing of neighbor bases, where d is 0.34 nm for double-stranded DNA. The experimenters use dyed contour length to refer to the fact that the dye-labelled DNA length under fluorescence observation is longer than its intrinsic contour length because of dye insertion into the DNA polymer chain. It should be appreciated that dye is not required in embodiments, but utilized for fluorescence observation. Under the experiment condition (a DNA base pair (bp) to dye ratio of 5:1 was used, or one dye inserted into every five bases), the additional extension is about 30%. The dyed contour length (L') is $L'=N \cdot d \cdot 1.3$. For example, for lambda DNA (48.5 kilo (k) base pairs), $L'=21.5$ micrometers (μm). For T4 DNA (~169 k bp), the $L'=75$ micrometers (μm). To compare the stretching efficiency accurately under fluorescence microscope, the experimenters use dyed contour length as the reference.

Location-specific straddling of DNA knows or determines in advance the locations at which straddling is to occur, where embodiments disclose that straddling occurs at interfaces between pillar regions (such as the interface of a larger pillar region and a smaller pillar region).

Embodiments provide a complete manufacturable nanofluidic chip integration scheme, including fabrication, packaging, and testing. The fabrication (only) requires standard photolithographic techniques without slow and expensive e-beam lithography to pattern deep nanoscale features (e.g., 30 nm) smaller than the DNA persistence length (e.g., 50 nm) for full DNA stretching, thus enabling future high-volume and low-cost production of DNA sensors. DNA persistence length is about 50 nm.

Now turning to the figures, FIGS. 1A, 1B, 1C, and 1D illustrate a schematic of a nanopillar array 100 that depicts a straddling mechanism according to an embodiment.

FIGS. 1A through 1D depict big diamond-shaped pillars and small diamond-shaped pillars. There is an interface between the big pillars and the small pillars. The interface is where the array of big pillars meets the small pillars. The fluidic flow drives the DNA to strongly interact with nanopillar structures (i.e., big and small nanopillars). For explanation purposes, only two pillar regions are shown to illustrate straddling, and it is appreciated that other pillar regions may be included before the big pillar region and/or after the small pillar region. Additionally, microblocks (not shown) may be included that provide microchannels for molecules to enter.

The DNA straddles one of the small pillars, such as straddle pillar 102 that is identified for example. It should be appreciated that other small pillars may act as the straddle pillar 102. When the DNA straddles the straddle pillar 102, one end of the DNA follows a first path and the other end of the DNA follows a second path. The first and second paths are different.

The high straddling occurrence rate is attributed to the nanostructure design of the nanopillar array 100 which guides the overall hydrodynamic flow parallel to the nanochannels but aligned 45° to the nanogaps between the diamond-shaped nanopillars (big pillars and small pillars), thus forcing DNA to follow a zig-zag path and to keep making 90° turns around the big and small pillars in order to increase the probability of a straddling interaction.

At the interface of the big and small pillar regions, the number of nanogap fluidic passages for possible DNA flow increases, and multiple DNA segments are more likely to simultaneously occupy orthogonal nanogaps (i.e., one nanogap along the first path and another nanogap along the second path) next to one pillar (i.e., the straddle pillar 102) to initiate the straddling depicted in FIGS. 1C and 1D.

Once the DNA starts the straddling in FIG. 1B (by having part of the DNA molecule simultaneously on both sides of the straddle pillar 102), the flow speed difference in the two pillar regions (higher in smaller pillar region versus big pillar region) quickly pulls the DNA head and tail forward (simultaneously) in the flow direction (in FIGS. 1C and 1D), hence applying a stress on the straddled DNA (middle) segment of the DNA molecule. The stress is on the straddled DNA segment that is pressed against the angle of the straddle pillar 102, and the angle of the straddled pillar 102 is at a 45° angle (e.g., using diamond-shaped pillars) to the nanogap of the big pillars. As such, the point of the straddled pillar 120 is positioned at the gap of the big pillars along the interface.

The nanopillars are small enough and allow straddling DNA molecule to be pulled tighter against the pillars (e.g., the straddle pillar 102) to keep the DNA from being immediately released. In addition, the smaller gaps in smaller pillar regions also help minimize the DNA molecule from coiling back. As a result, the straddling effectively stretches the DNA as shown from FIG. 1B, to FIG. 1C, to FIG. 1D. This results in a stretched DNA molecule.

FIG. 1E is a graph illustrating DNA flow speed change at the pillar interface according to an embodiment. In FIG. 1E, an example is provided to show the DNA flow speed change (in relative values) as the DNA molecule traverses from one pillar region (e.g., the big pillar region) to another region (e.g., the small pillar region).

The reason for the designed flow speed change is because in a fluidic volume conserved nanofluidic system, the fluidic volume flowing across any region at a given time should be identical, regardless of what the nano-confinement dimension is. Therefore, the flow speed changes as the allowed cross-sectional area changes in different patterned regions.

Figure 2:
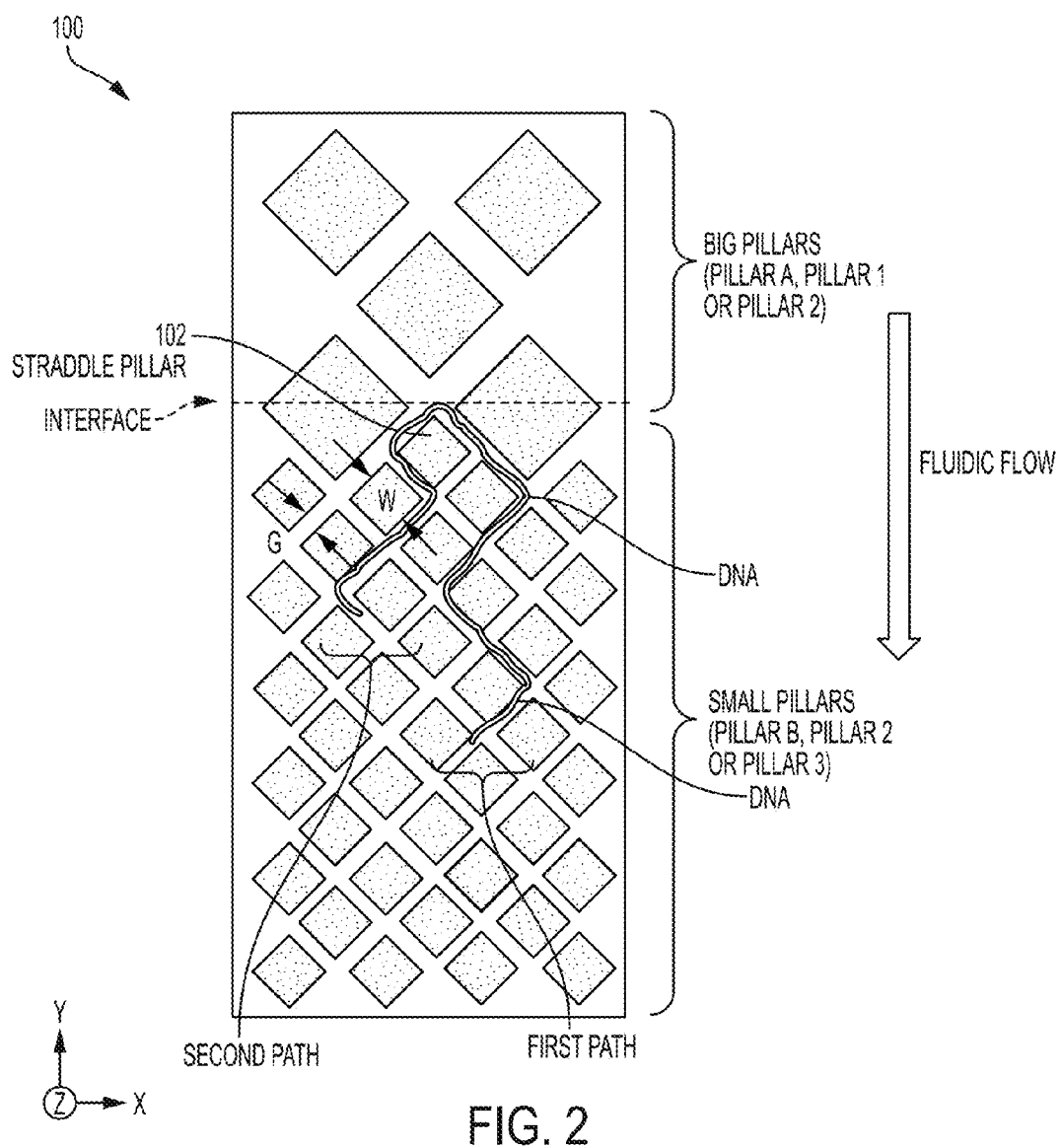
FIG. 2 is a schematic of the nanopillar array illustrating an application of stretching a long molecule according to an embodiment.

FIG. 2 is a schematic of the nanopillar array 100 illustrating an application of stretching long DNA according to an embodiment. In the straddling mechanism, the designed dimension of pillar width W is related to the DNA length L. The DNA length L is to be much larger than 2·W to induce effective straddling in which the DNA molecule is pulled tight enough to the small pillars (e.g., the straddling pillar 102) in hydrodynamic flow.

In an experiment, the dye-labelled λ-DNA (48.5 kilo base pairs (kbp)) length is 30% longer than its intrinsic contour length without dye. In other words, the contour length observed under fluorescence imaging for the λ-DNA is about 21.5 μm, taking into account the 30% additional stretch produced by the insertion of the dye. The experimenters have determined that the straddling on 1.55 micron (μm) pillars (which are small pillars such as the straddle pillar 102) are very effective, with a gap size G=240 nm between the small pillars in the small pillar region.

In the state-of-the-art, the persistence length of double-stranded λ-DNA (50 nm) requires geometric confinement to stretch DNA that would require the gap to be less that (<) 50 nm for their small pillars. The state-of-the-art nanopillar array cannot use a gap size G=240 nm for the small pillar region.

In accordance with an embodiment, this shows that the structure design of the nanopillar array 100 has a working principle that effectively stretches DNA molecules without making the gap and pillar size in the small pillar region very small (e.g., gap size G=240 nm and pillar width 1.55 μm can be utilized in the small pillar region). In contrast, the state-of-the-art has pillars and gaps that need to be comparable to the nanochannels at the channel entrance.

It is assumed that the straddling efficiency remains unchanged when scaling linearly the DNA length, the pillar width W, and gap size G. Extrapolated/estimated pillar widths W and channel gap G in the small pillar region for stretching long DNA molecules is provided:

For 100 kilo base pair (DNA length): small pillar width W=(approximately) 3.2 μm, and small pillar gaps G=0.5 μm in the small pillar region.

For 1 million base pair (DNA length): small pillar width W=(approximately) 32 μm, and small pillar gaps G=5 μm in the small pillar region.

For 10 million base pair (DNA length): small pillar width W=(approximately) 320 μm, and small pillar gaps G=50 μm in the small pillar region.

In embodiments, it should be recognized that the pillar width and gap size are beneficial in the nanopillar array 100 for at least the following reasons. (1) Long DNA stretching is very useful for genome analysis, but the state-of-the-art still needs very small gaps<50 nm (DNA persistence length) for full stretching. (2) In embodiments, the pillar widths W and gap sizes G can be designed large, so that the pillars can be printed by inexpensive photolithography without expensive nanofabrication, thereby greatly reducing the fabrication cost.

FIG. 2 also shows an example in which the big pillar width W is 3 μm, and the big pillar gaps are G=550 nm.

FIGS. 3A, 3B, 3C, 3D, 3E, and 3F illustrate a fabrication scheme of an example nanopillar array 100 according to an embodiment. It should be appreciated that more features of shown in FIGS. 4A through 4F.

Figure 3C:
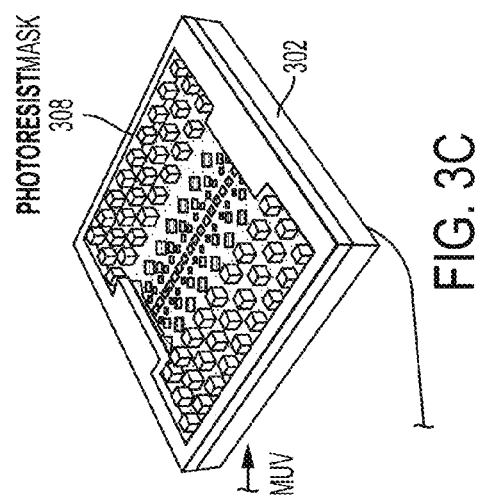
Figure 3B:
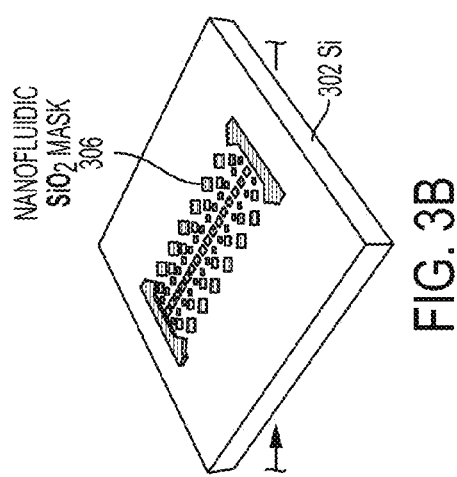
Figure 3A:
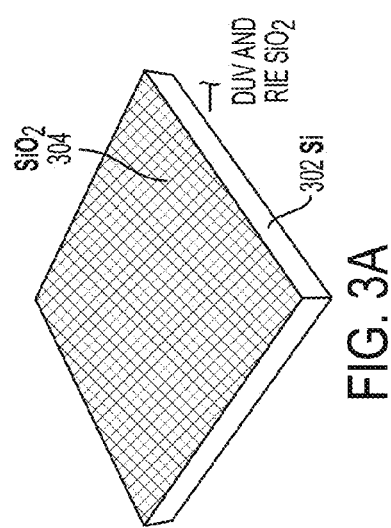

FIG. 3A is a schematic of an intermediate structure illustrating a substrate 302 with an oxide layer 304 disposed on top. The material of substrate 302 may be a silicon, germanium, etc. The oxide layer 304 may be silicon dioxide or another oxide material. In one implementation, the layer 304 may be a nitride.

FIG. 3B is a schematic of the intermediate structure illustrating a nanofluidic mask 306 etched into the oxide layer 304. FIG. 3B shows nano-patterned nanofluidic features in the silicon dioxide by, e.g., deep ultraviolet (DUV) lithography and reactive ion etching (RIE). To pattern the nanofluidic mask 306, the oxide layer 304 may be exposed with light, e.g., deep ultraviolet (DUV) exposure via photolithography, according to the desired pattern. In one case, the exposed portion of the oxide layer 304 may be etched to leave the nanofluidic mask 306. In another case, the unexposed portion of the oxide layer 304 may be etched to leave the nanofluidic mask 306.

FIG. 3C is a schematic of the intermediate structure illustrating disposing and patterning a photoresist mask 308. The micro-patterned photoresist mask 308 is aligned to nanofluidic features of the nanofludic mask 306. The photoresist may be disposed on top of the substrate 302 and the nanofludic mask 306. Lithographic patterning methods, such as middle ultraviolet (MUV) exposure, may be utilized to form the desired micro-pattern in the photoresist via photolithography, and the unexposed portion of the photoresist is etched away to leave the photoresist mask 308.

FIG. 3D is a schematic of the intermediate structure illustrating use of the nanofludic mask 306 and photoresist mask 308 to etch microchannels 314 and nanochannels 301 into substrate 302, along with (pre) pillars 323, 325, 327 and (pre) microblocks 312. FIG. 3D shows connected shallow microfluidic and nanofluidic systems etched into the silicon substrate 302, after the photoresist mask 308 and nanofluidic mask 306 are stripped.

FIG. 3E is a schematic of the intermediate structure illustrating deep microchannels 316 formed inside the shallow microchannel 314 by a second series of lithography to pattern a photoresist mask, etch the substrate 302 according to the photoresist mask, and strip the photoresist mask.

FIG. 3F is a schematic of the nanopillar array 100 illustrating an oxide layer 318 conformally disposed on the substrate 302. The nanopillar array 100 has microchannels 320 between the microblocks 334, pillars 324, pillars 326, and pillars 328. Also, the nanopillar array 100 includes nanochannels 322 fluidly connected to the pillars 324.

Pillars 328 have a larger width than pillars 326. Pillars 326 have a larger width than pillars 324. Similarly, the gap separating pillars 328 from one another is larger than the gap separating pillars 326 from one another. Also, the gap separating pillars 326 from one another is larger than the gap separating pillars 324 from one another.

FIGS. 4A, 4B, 4C, 4D, 4E, and 4F illustrate scanning electron microscope (SEM) images showing fabricated microfluidic and nanofluidic structures according to an embodiment. FIGS. 4A through 4F are a fabricated nanofludic structure, such as, representative of the nanopillar array 100. It should be appreciated that more features of shown in FIGS. 4A through 4F.

Figure 4B:
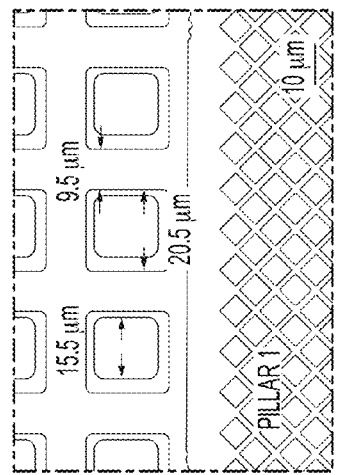
FIGS. 4A, 4B, 4C, 4D, 4E, and 4F illustrate scanning electron microscope (SEM) images of a nanopillar array according to an embodiment.
Figure 4D:
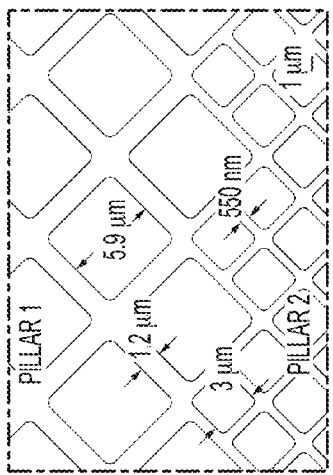
Figure 4F:
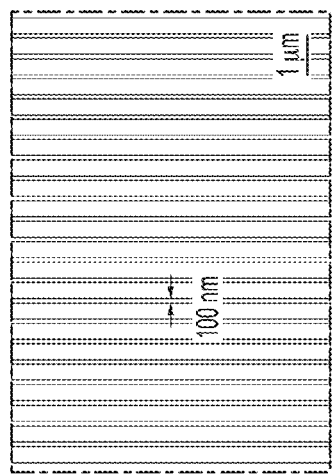
Figure 4A:
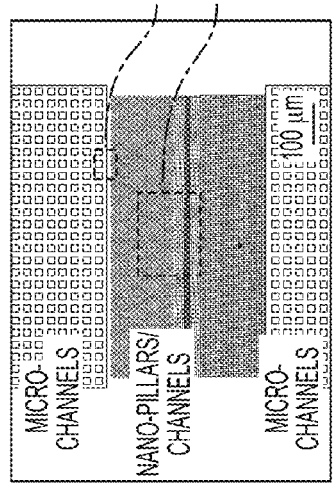

FIG. 4A illustrates a low-magnification image showing the connection of microchannels to nanofluidic channels and showing diamond-shaped nanopillars.

FIG. 4B illustrates a zoomed-in image at the interface of microchannels (with 15.5 μm wide shallow pillars and 20.5 μm wide deep pillars) and nanopillars (pillar region 1).

Figure 4C:
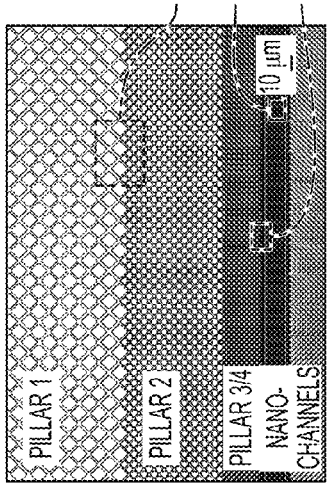

FIG. 4C illustrates a zoomed-in image showing nanofluidic integration of nanochannels with four different diamond-shaped pillar regions (e.g., pillar regions 1, 2, 3, and 4).

FIG. 4D illustrates a high-magnification image at the interface of pillar region 1 (5.9 μm pillar width and 1.2 μm gap) and pillar region 2 (3 μm pillar width and 550 nm gap).

Figure 4E:
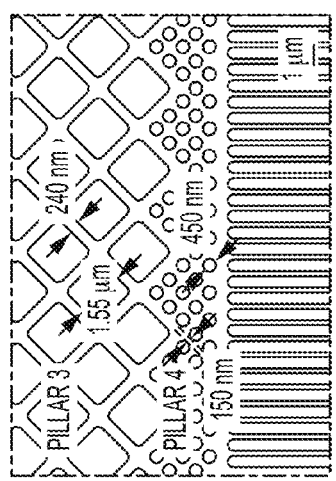

FIG. 4E illustrates a high-magnification image showing pillar region 3 (1.55 μm pillar width and 240 nm gap), pillar 4 (450 nm pillar width and 150 nm gap), and nanochannels.

FIG. 4F illustrates a high-magnification image showing uniform 100 nm wide nanochannels at a 500 nm pitch. The nanochannel pitch is the distance between the center of a nanochannel wall to the center of the next nanochannel wall.

Figures 5A, 5B:
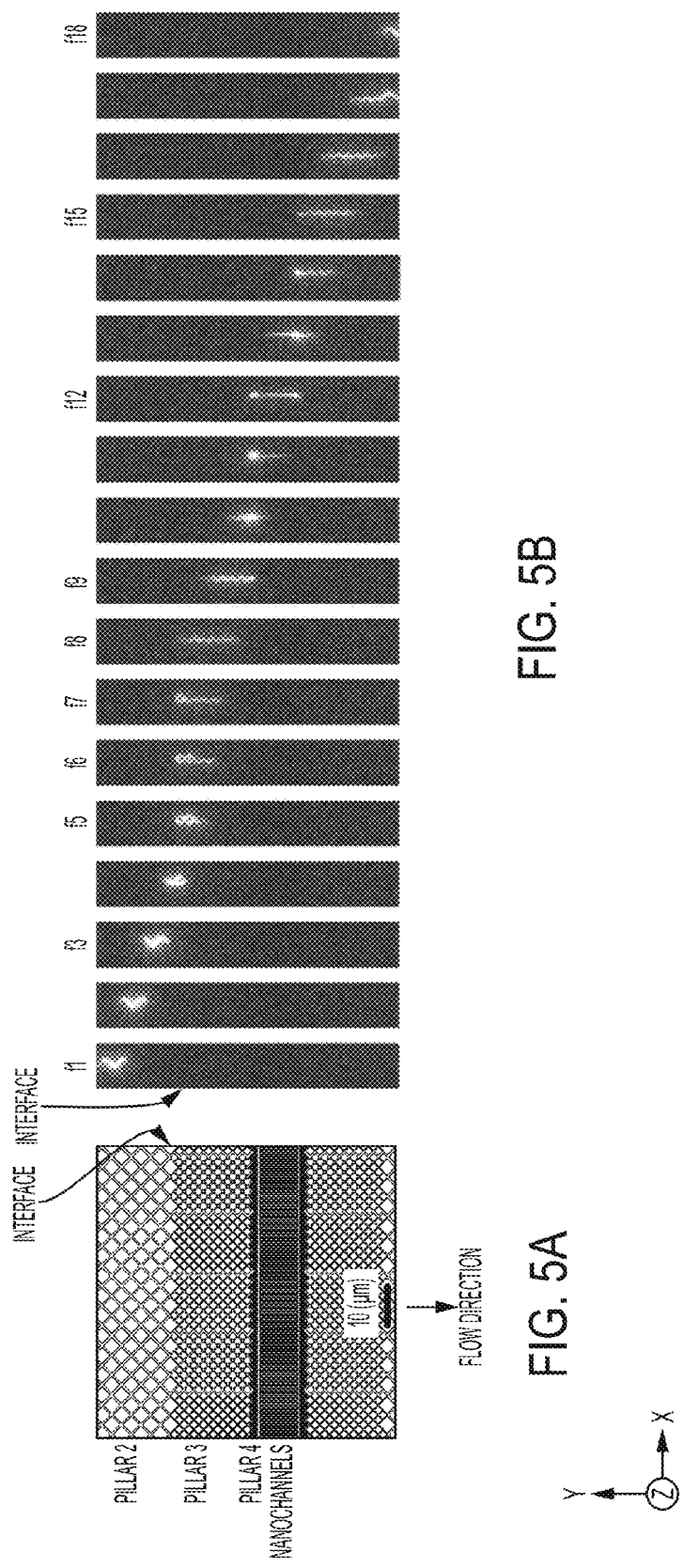
FIG. 5A is a scanning electron microscope (SEM) image of a nanopillar array illustrating pillar regions 2, 3, and 4 according to an embodiment.
FIG. 5B illustrates consecutive fluorescence images of a DNA molecule flowing through nanopillar array in FIG. 5A according to an embodiment.

FIG. 5A is a scanning electron microscope (SEM) image of a nanopillar array (such as nanopillar array 100) showing pillar region 2 meeting pillar region 3 at the interface, along with pillar region 4 and nanochannels according to an embodiment.

FIG. 5B is a scanning electron microscope image of a λ-DNA molecule flowing through the nanopillar array in FIG. 5A. In FIG. 5A, the SEM image is of the nanofluidic region corresponding to fluorescence images. The channels are 100 nm wide, 180 nm deep, and 500 nm in pitch.

FIG. 5B illustrates consecutive fluorescence images (frames f1-f18) showing the λ-DNA molecule flowing through nanofluidic regions, with a frame rate of 49.3 hertz (Hz). Frame f5 shows the beginning of the straddling (such as, e.g., straddling around the straddling pillar 102) of the DNA molecule because of the interface between pillar region 2 and pillar region 3. Frame f6 shows how the straddling stretches the DNA molecule along two different paths (e.g., first path and a second path around the straddling pillar 102). Frame f7 shows further stretching of the DNA molecule because of the straddling. Frame f8 shows the stretched DNA that has been stretched to greater than 90% of its dyed contour length.

Figure 5C:
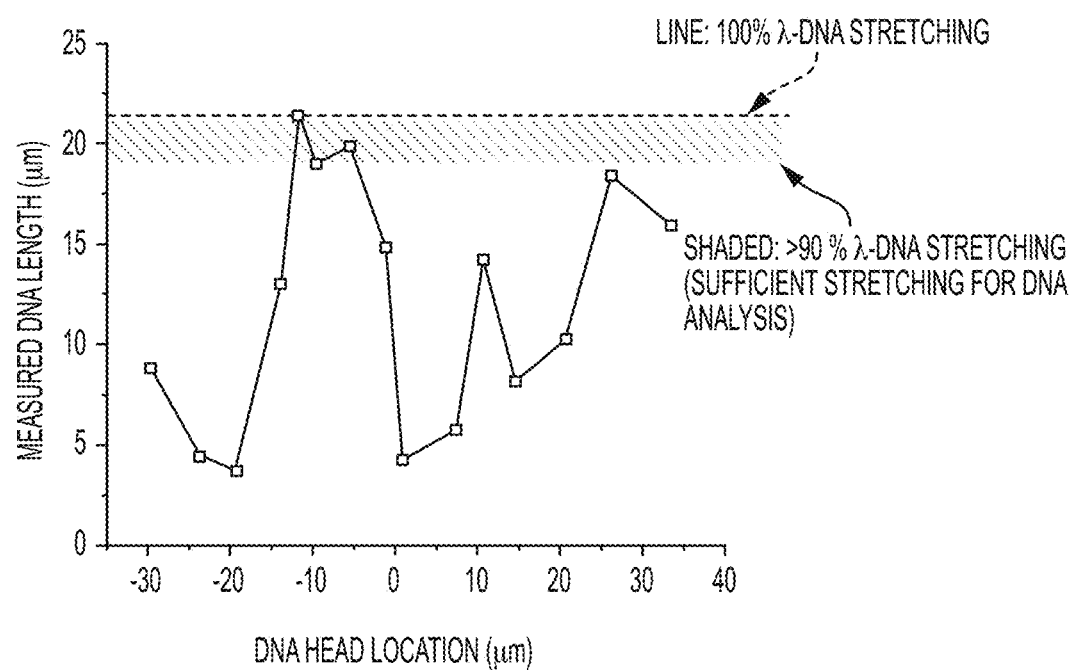
FIG. 5C is a graph of measured DNA length to illustrate straddling by the DNA molecule according to an embodiment.

FIG. 5C is a graph of measured DNA length on the y-axis versus DNA head location on the x-axis. FIG. 5C shows that because of the straddling the DNA achieves greater than 90% stretching of its dyed contour length.

Figure 6B:
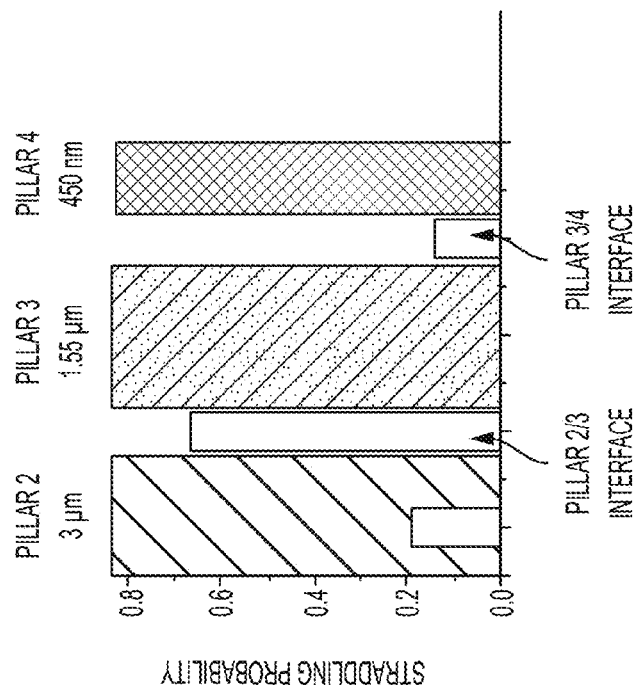
FIG. 6B is a graph illustrating straddling probability at the different positions of pillar regions according to an embodiment.
Figure 6A:
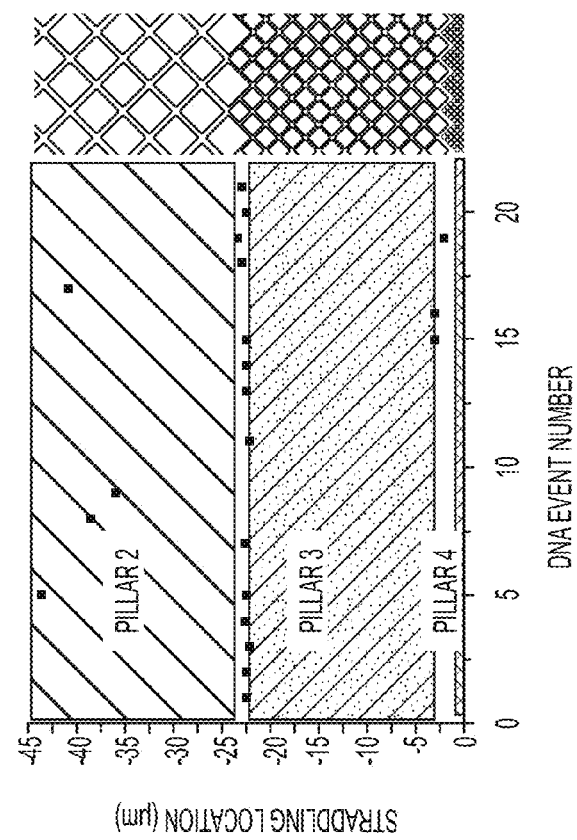
FIG. 6A is a graph illustrating the straddling location according to an embodiment.

FIGS. 6A and 6B illustrate location-specific DNA straddling. FIG. 6A is a graph illustrating the straddling location in the nanopillar array (in FIGS. 5A, 5B) and FIG. 6B is a graph illustrating straddling probability at the interface of pillar regions 2 and 3, and the interface of pillar regions 3 and 4.

To unveil the DNA-nanopillar hydrodynamic interactions, the experimenters used single-molecule fluorescence analysis to image translocation of double-stranded λ-DNA (48.5 kb, contour length (approximately) 21.5 μm with labelled fluorescence dye). As the DNA molecules were driven into the nanofluidic system by pressure gradient, the DNA molecules were observed to collide with and temporarily straddle nanopillars during translocation as depicted in FIG. 5A.

Out of 21 randomly selected λ-DNA events with the DNA speed and extension mapped to the nanostructure locations, 18 molecules (86%) were found to straddle pillars. Particularly, the single-molecule analysis revealed location-specific straddling behavior, i.e., 78% of straddling events (67% of all mapped 21 DNA events) occurred at the interface of pillar regions 2 and 3 in FIG. 6B where the pillar width changes from approximately 3 μm (in pillar region 2) to 1.55 μm (in pillar region 3). Such a high straddling occurrence rate and a (consistent) location-specific behavior determine that nanopillars can significantly alter the DNA hydrodynamic flow and induce controlled DNA stretching according to embodiments.

To show location-specific λ-DNA straddling during translocation in FIG. 6A, the DNA straddling location is scatter-plotted against the DNA event occurrence using the nanochannel entrance as the location reference. In FIG. 6A, the DNA molecules are marked on the plot, and the corresponding SEM image of the nanostructure is shown on the right.

FIGS. 7A and 7B illustrate DNA stretching efficiency comparison according to an embodiment. Single-molecule analysis is discussed.

FIG. 7A is a graph illustrating the percentage of maximum stretching for DNA flowing through the nanopillars with straddling at the interface and for DNA molecules flowing through the nanopillars without experiencing any straddling for the number of observed DNA flow events.

FIG. 7B is a graph illustrating DNA stretching by straddling at the pillar interface (of pillar regions 2 and 3) has a high stretching efficiency (greater than (>) 91% on average for all DNA). The DNA stretching efficiency as they flow through pillars without straddling is approximately 42% on average. Each of the measured DNA lengths at straddling is averaged from consecutive fluorescence images, starting from straddling initiation to the DNA molecule being released. The DNA lengths without straddling are measured during flow in the nanopillar regions, and only the events that are free of impact by straddling are analyzed.

The stretching of DNA facilitates the translocation of DNA molecules through nanochannels. Embodiments provide a method and apparatus to stretch DNA molecules using pillar interfaces (e.g., the pillar interface at pillar regions 2 and 3) in route to translocation through nanochannels. The use of pillar interfaces for straddling is not disclosed in the state-of-the-art, and embodiments provide quantitative improvements to DNA stretching.

According to an embodiment, the experimenters observed the high-probability of straddling and location specific straddling: in the single-molecule analysis, the experimenters determined that a majority of the DNA molecules (18 out of 21 mapped events) collided with and temporarily straddled pillars (such as one or more straddling pillars 102) during translocation through the nanopillars and nanochannels within the imaged area. Approximately 80% of the DNA straddling events (14 out of 18) occurred at the pillar region 2 to pillar region 3 interface where the pillars change pillar width from 3 μm (in pillar region 2) to 1.55 μm (pillar region 3).

According to an embodiment, there is a higher DNA stretching efficiency upon straddling: DNA straddled at an interface stretches on average to a length twice as long (100% longer) than DNA not-straddling (i.e., from 42% of its contour length to 91% of its contour length).

Taken together, the previous observations mean that a majority of DNA molecules straddle and consequently stretch to twice as long (to about 90% of its contour length) when their microfluidic structures contain rationally designed pillar interfaces. This means that there is a quantitative increase in the efficiency of the stretching using nanopillars arrays with designed pillar interface. Such a stretching is also necessary to avoid clogging (at the nanochannels) and facilitate translocation.

FIGS. 8A, 8B, and 8C depict T4 DNA translocation through nanochannels without clogging. T4 DNA is longer than the λ-DNA discussed above to show that straddling works to stretch short and longer DNA molecules.

FIG. 8A is a schematic of a nanopillar array, such as nanopillar array 100. FIG. 8A shows that straddling can keep DNA in stretched form, and facilitate DNA translocation and stretching in nanochannels.

FIG. 8B illustrates fluorescent images of the DNA travelling through the nanopillar array. To reveal the detailed interactions of T4 DNA with the nanopillars and nanochannels at the high speed, experimenters captured the translocation events of single T4 DNA molecules at 300 Hz by reducing recorded imaging area sizes in FIG. 8B. Similar to λ-DNAs, T4 DNAs can straddle nanopillars under hydrodynamic flow; as a result, the T4 DNA even stretches to close to its full dye-labeled contour length (approximately 73.5 μm, which is approximately 30% longer than unlabeled length about 56 μm), as shown in frames 21-36 and 51-101 in FIG. 8B.

With reference to the graph in FIG. 8C, the temporal hydrodynamic interaction can be understood by plotting the DNA head/tail location and extension length as a function of time or frame. Evidently, during straddling interactions (shaded time frame), the tail first moved forward following hydrodynamic flow, but then turned backward as the head managed to lead the molecule forward over the straddled pillars (such as, e.g., straddled pillars 102), similar to pulling a rope on a pulley. The pulling process along the pillars extended the T4 DNA to 73.5 μm, i.e., approximately 100% stretched. Then, immediately after being released from the anchored pillar (e.g., the straddled pillar 102), the DNA tail was found to move faster than the head, and as a result the DNA relaxed to a shorter length. This relaxation effect is believed to be caused by the entropic force. This process, akin to pulling a rope on a pulley, is utilized to stretch shorter DNA molecules (e.g., λ-DNA) and long DNA molecules (e.g., T4 DNA) according to embodiments.

Compared to λ-DNA, T4 DNA is much longer and more prone to interact with nanofluidic structures and accordingly has a more complex translocation behavior. Because of such extensive hydrodynamic interactions, T4 DNA molecules were found to straddle pillars and extend to 65.8 μm or 90% of its dye-labeled contour length even at a low speed of approximately 20 μm/sec. This shows the benefit of controlling pillar dimensions to induce appropriate interaction and linearize a DNA molecule at a slow speed, which is particularly interesting for precise location control and sensing.

FIGS. 9A, 9B, and 9C depict straddling induced stretching that helps reduce clogging of long DNA in nanochannels according to an embodiment. FIGS. 9A, 9B, and 9C relate to T4 DNA translocation through a 30 nm wide nanochannel and nanopillars.

FIG. 9A is a scanning electron microscope image of a nanopillar array (such as nanopillar array 100), which shows nanopillars and nanochannels. FIG. 9B is a scanning electron image of nanochannels in the nanochannel region. The channels are 5 μm long, 50 nm deep, and 500 nm in pitch.

FIG. 9C illustrates consecutive fluorescence images showing DNA translocation, with a frame rate of 54 Hz. The dashed lines indicate the locations of nanochannels.

With regard to pre-stretching to reduce clogging in nanochannels, all λ-DNA molecules were observed to translocate through the 10 µm long nanochannels in a short time (average 68 millisecond (msec)±20 msec) and no clogging was observed during operation. In the state-of-the-art, one challenge in nanopore DNA sensing is the difficulty of controlling the translocation speed and time for reliable reading, because the lack of effective geometrical confinement and pre-stretching elements in nanopores results in a high entropic barrier for DNA to translocate and also cause random DNA events prior to and during translocation, such as pore blockage, folded-entry, retraction from pores, etc. In comparison, the patterned nanopillars in embodiments can pre-stretch the DNA molecules through straddling interactions to reduce the entropic barrier, geometrically confine the DNA location, and minimize DNA recoiling at the nanochannel entrance vicinity, therefore greatly enhancing the rate of capturing DNA and uniform translocation, which is desirable in electrical sensing for precisely controlling DNA speed and location.

With the effective straddling mechanism in embodiments, even longer T4 DNA molecules were found to translocate through both 100 nm wide and 30 nm wide nanochannels. This demonstrates that the fabrication scheme in embodiments is capable of tuning nanofluidic feature dimensions smaller than the DNA persistence length (e.g., DNA persistence length 50 nm), which is particularly important to stretching DNA to eliminate DNA coiling for genomic mapping and reliable electrical sensing. Oxidation and/or conformal deposition of dielectric materials help further shrink the feature dimensions to sub-10 nm, which is utilized for electrical detection of DNA.

Figure 10:
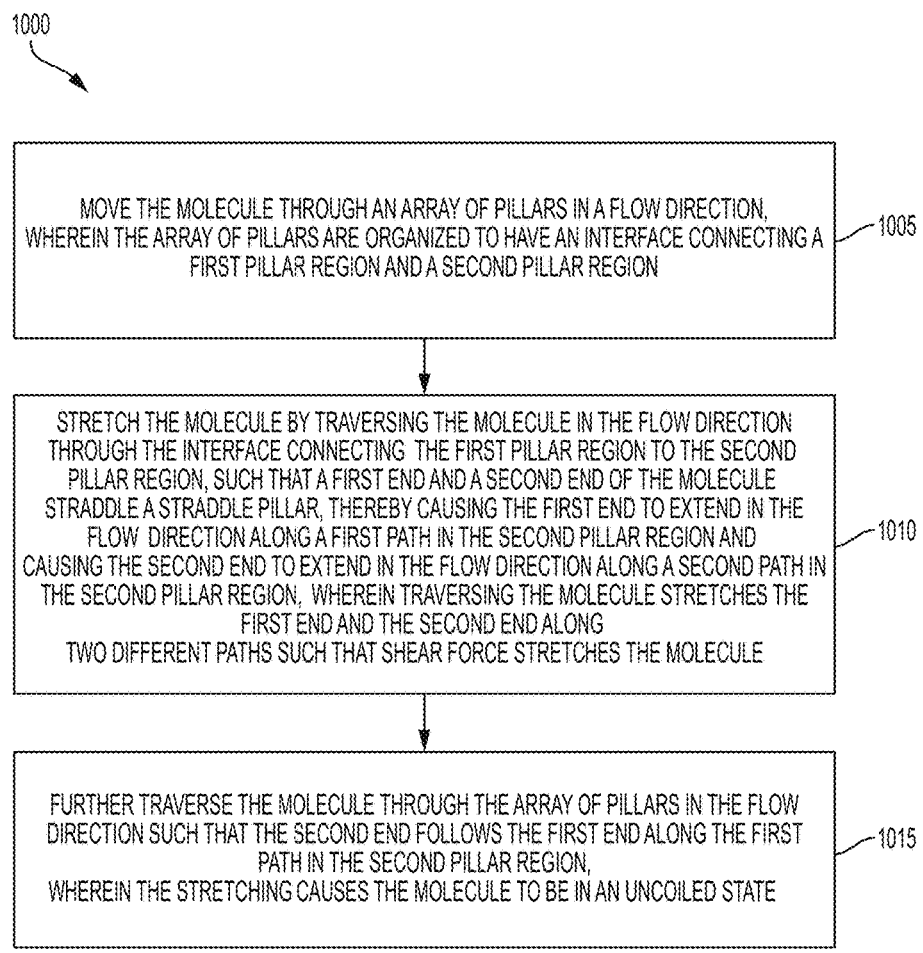
FIG. 10 is a flow chart of a method to stretch a molecule flowing in a fluidic device according to an embodiment.

FIG. 10 is a flow chart of a method to stretch an extensible molecule flowing in a fluidic device according to an embodiment.

At block 1005, the molecule (e.g., DNA or RNA molecule) is moved through an array of pillars in a flow direction, wherein the array of pillars are organized to have an interface connecting a first pillar region (e.g., big pillar region, pillar region 1, or pillar region 2) and a second pillar region (small pillar region, pillar region 2 (when first pillar region is pillar region 1), or pillar region 3 (when first pillar region is pillar region 2)). The molecule may enter microchannels, such as microchannels 320 in FIG. 3 and/or microchannels in FIG. 4A, to reach the array of pillars.

At block 1010, the molecule is stretched by traversing the molecule in the flow direction through the interface connecting the first pillar region to the second pillar region, such that a first end and a second end of the molecule straddle a straddle pillar (such as, e.g., straddle pillar 102), thereby causing the first end to extend in the flow direction along a first path in the second pillar region and causing the second end to extend in the flow direction along a second path in the second pillar region, wherein traversing the molecule stretches the first end and the second end along two different paths. Reference can be made to the molecule in FIGS. 1B, 1C, 1D, 2, 5B, 8A, 9C. To observe the DNA straddling and cause the consequent stretching, hydrodynamically induced polymer (DNA) flow (by applying an external pressure gradient as the driving force) and/or electrophoretically induced polymer (DNA) flow (by applying an external electric field gradient as the driving force) may be used.

At block 1015, further traversing the molecule through the array of pillars in the flow direction such that the second end follows the first end along the first path in the second pillar region, wherein the stretching causes the molecule to be in an uncoiled state. Reference can be made to the molecule in FIGS. 1B, 1C, 1D, 2, 5B, 8A, 9C.

The first pillar region is homogeneous, and the second pillar region is homogeneous. The pillars in the first and second pillar regions may be a diamond shape. In other implementations, the pillars may be triangular, parallelogram, or round. The first pillar region includes first pillars having a first width and the second pillar region includes second pillars having a second width. The first width (e.g., 3 µm) of the first pillars is larger than the second width (e.g., 1.55 µm) of the second pillars. The flow direction is from the first pillar region to the second pillar region (e.g., in the y-axes).

The straddle pillar (such as, e.g., one or more straddle pillars 102) is in the second pillar region. Straddling of the straddle pillar occurs as the molecule is leaving the first pillar region and entering the second pillar region. The interface between the first and second pillar regions in discontinuous, such that the interface is jagged.

Figure 11:
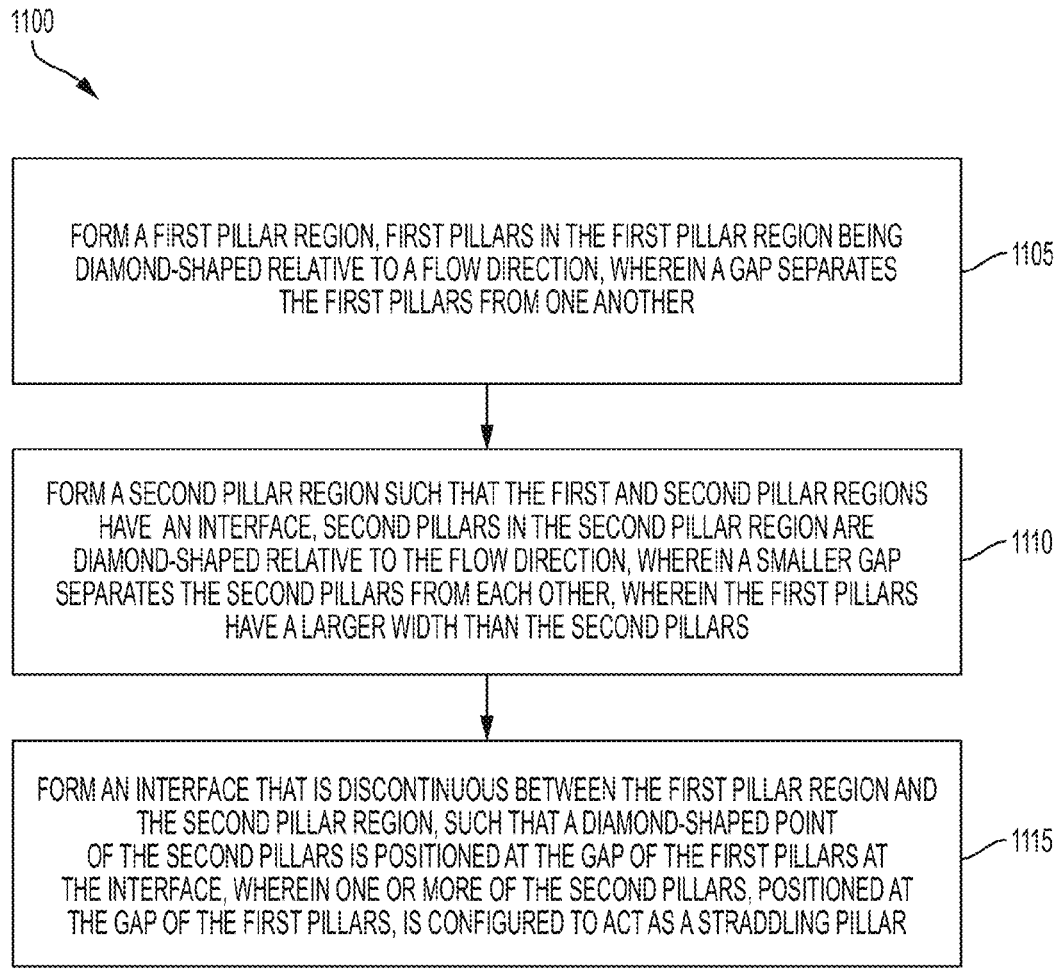
FIG. 11 is a flow chart of a method of fabricating an array of pillars to cause straddling according to an embodiment.

FIG. 11 is a flow chart of a method of fabricating an array of pillars to cause straddling according to an embodiment.

At block 1105, a first pillar region is formed in which first pillars in the first pillar region are diamond-shaped relative to a flow direction, where a gap separates the first pillars from one another.

At block 1110, a second pillar region is formed such that the first and second pillar regions have an interface, where the second pillars in the second pillar region are diamond-shaped relative to the flow direction, where a smaller gap separates the second pillars from each other, where the first pillars have a larger width than the second pillars.

At block 1115, an interface that is discontinuous is formed between the first pillar region and the second pillar region, such that a diamond-shaped point of the second pillars is positioned at the gap of the first pillars at the interface, where one or more of the second pillars, positioned at the gap of the first pillars, are configured to act as a straddling pillar.

On an opposite side of the second pillar region relative to the first pillar region, nanochannels are formed. One or more other pillars regions are formed between the second pillar region and the nanochannels.

In one implementation, the gap may be twice as large as the smaller gap. A first width of the first pillars may be twice as large as a second width of the second pillars. Reference can be made to pillar region 2 versus pillar region 3 in FIGS. 4D and 4E. It should be appreciated that other ratios care also possible.

The molecule is a DNA or RNA molecule of length at least 10 times the second width of the second pillars.

It will be noted that various microelectronic device fabrication methods may be utilized to fabricate the components/elements discussed herein as understood by one skilled in the art. In semiconductor device fabrication, the various processing steps fall into four general categories: deposition, removal, patterning, and modification of electrical properties.

Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), and chemical-mechanical planarization (CMP), etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution. After etching or other processing, the remaining photoresist is removed. Patterning also includes electron-beam lithography.

Modification of electrical properties may include doping, such as doping transistor sources and drains, generally by diffusion and/or by ion implantation. These doping processes are followed by furnace annealing or by rapid thermal annealing (RTA). Annealing serves to activate the implanted dopants.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method to stretch an extensible molecule flowing in a fluidic device, the method comprising:
    moving a molecule through an array of pillars in a flow direction, wherein the array of pillars are organized to have at least one interface connecting a first pillar region and a second pillar region;
    stretching the molecule by traversing the molecule in the flow direction through the interface connecting the first pillar region to the second pillar region, such that a first end and a second end of the molecule straddle at least one straddle pillar, thereby causing the first end to extend in the flow direction along a first path in the second pillar region and causing the second end to extend in the flow direction along a second path in the second pillar region, wherein traversing the molecule stretches the first end and the second end along two different paths; and
    further traversing the molecule through the array of pillars in the flow direction such that the second end follows the first end along the first path in the second pillar region, wherein the stretching causes the molecule to be in an uncoiled state;
    wherein the interface between the first and second pillar regions is discontinuous, such that the interface is jagged.

2. The method of claim 1, wherein the first pillar region is homogeneous.

3. The method of claim 1, wherein the second pillar region is homogeneous.

4. The method of claim 1, wherein pillars in the first and second pillar regions are a diamond shape.

5. The method of claim 1, wherein the first pillar region includes first pillars having a first width and the second pillar region includes second pillars having a second width.

6. The method of claim 5, wherein the first width of the first pillars is larger than the second width of the second pillars.

7. The method of claim 6, wherein the flow direction is from the first pillar region to the second pillar region.

8. The method of claim 7, wherein the straddle pillar is in the second pillar region.

9. The method of claim 8, wherein straddling of the straddle pillar occurs as the molecule is leaving the first pillar region and entering the second pillar region.

10. The method of claim 5, where the molecule is a DNA or RNA molecule of length at least 10 times the second width of the second pillars.

11. A fluidic device having an array of pillars to cause straddling, the device comprising:
    a first pillar region of first pillars, wherein a gap separates the first pillars from one another;
    a second pillar region of second pillars such that the first and second pillar regions have an interface, wherein a smaller gap separates the second pillars from each other, wherein the first pillars have a larger width than the second pillars; and
    an interface that is discontinuous between the first pillar region and the second pillar region, such that a point of the second pillars is positioned at the gap of the first pillars at the interface, wherein one or more of the second pillars, positioned at the gap of the first pillars, is configured to act as a straddling pillar.

12. A method of fabricating an array of pillars to cause straddling, the method comprising:
    forming a first pillar region of first pillars, wherein a gap separates the first pillars from one another;
    forming a second pillar region of second pillars such that the first and second pillar regions have an interface, wherein a smaller gap separates the second pillars from each other, wherein the first pillars have a larger width than the second pillars; and
    forming an interface that is discontinuous between the first pillar region and the second pillar region, such that a point of the second pillars is positioned at the gap of the first pillars at the interface, wherein one or more of the second pillars, positioned at the gap of the first pillars, is configured to act as a straddling pillar.

13. The method of claim 12, wherein on an opposite side of the second pillar region relative to the first pillar region, nanochannels are formed.

14. The method of claim 13, wherein one or more other pillars regions are formed between the second pillar region and the nanochannels.

15. The method of claim 10, wherein the first pillars in the first pillar region and the second pillars in the second pillar region are diamond-shaped relative to a flow direction.

16. The device of claim 11, wherein on an opposite side of the second pillar region relative to the first pillar region, nanochannels are formed.

17. The device of claim 16, wherein one or more other pillars regions are formed between the second pillar region and the nanochannels.

18. The device of claim 11, wherein the first pillars in the first pillar region and the second pillars in the second pillar region are diamond-shaped relative to a flow direction.

19. The device of claim 11, wherein the gap is twice as large as the smaller gap; and
   wherein a first width of the first pillars is twice as large as a second width of the second pillars.

* * * * *